United States Patent
Shigemori et al.

(10) Patent No.: US 8,038,608 B2
(45) Date of Patent: Oct. 18, 2011

(54) BODY-CAVITY IMAGE OBSERVATION APPARATUS (75) Inventors: Toshiaki Shigemori, Tokyo (JP); Akira Matsui, Tokyo (JP)

(73) Assignees: Olympus Corporation (JP); Olympus Medical Systems Corporation (JP)

( * ) Notice: Subject to any disclaimer, the term of this patent is extended or adjusted under 35 U.S.C. 154(b) by 1230 days.

(21) Appl. No.: 11/573,337

(22) PCT Filed: Sep. 8, 2006

(86) PCT No.: PCT/JP2006/317865
§ 371 (c)(1),
(2), (4) Date: Feb. 6, 2007

(87) PCT Pub. No.: WO2007/029815
PCT Pub. Date: Mar. 15, 2007

(65) Prior Publication Data
US 2009/0259096 A1 Oct. 15, 2009

(30) Foreign Application Priority Data
Sep. 9, 2005 (JP) .................................. 2005-263091

(51) Int. Cl.
*A61B 1/06* (2006.01)
(52) U.S. Cl. ....................................................... 600/160
(58) Field of Classification Search .................. 600/101, 600/109, 118, 117, 160; 348/65, 72–75
See application file for complete search history.

(56) References Cited

U.S. PATENT DOCUMENTS

| 6,602,185 | B1 * | 8/2003 | Uchikubo | 600/118 |
| 7,662,090 | B2 * | 2/2010 | Obata | 600/118 |
| 2002/0173718 | A1 | 11/2002 | Frisch et al. | |
| 2003/0020810 | A1 | 1/2003 | Takizawa et al. | |

(Continued)

FOREIGN PATENT DOCUMENTS

JP 2003-19111 1/2003

(Continued)

OTHER PUBLICATIONS

International Preliminary Report in Japanese with cited references for PCT Appln. No. PCT/JP2006/317865 dated Dec. 12, 2006.

(Continued)

*Primary Examiner* — Philip Smith
(74) *Attorney, Agent, or Firm* — Ostrolenk Faber LLP (57) ABSTRACT

An object of the present invention is to enable clearly identifying whether a body-cavity image displayed on a display unit is based on data which is directly received by a viewer itself, or whether the body-cavity image displayed on the display unit is based on data received by another receiving device. An identification notifying unit presents different identification modes such as a capsule mark and a cable mark 41 which are sensory recognizable between the case where a body-cavity image based on body-cavity image data which a first receiving unit has received directly from a capsule endoscope is displayed, and the case where a body-cavity image 40 based on body-cavity image data which a second receiving unit has received via another receiving device is displayed. Thus, it is possible to clearly identify which receiver has received the body-cavity image data based on which the body-cavity image is displayed.

4 Claims, 9 Drawing Sheets

U.S. PATENT DOCUMENTS

| | | | |
|---|---|---|---|
| 2003/0023150 A1 | 1/2003 | Yokoi et al. .................... | 600/300 |
| 2003/0043263 A1 | 3/2003 | Glukhovsky et al. | |
| 2004/0225185 A1* | 11/2004 | Obata et al. .................... | 600/118 |
| 2004/0230094 A1* | 11/2004 | Nakamura .................... | 600/101 |
| 2004/0249291 A1 | 12/2004 | Honda et al. .................... | 600/476 |
| 2005/0148816 A1 | 7/2005 | Glukhovdsky et al. | |
| 2006/0202998 A1 | 9/2006 | Hirakawa et al. | |

FOREIGN PATENT DOCUMENTS

| | | |
|---|---|---|
| JP | 2005-218584 | 8/2005 |
| JP | 2006-288543 | 10/2006 |
| WO | WO 01/87377 | 11/2001 |
| WO | WO 2005/004033 | 1/2005 |

OTHER PUBLICATIONS

Australian Office Action dated Apr. 6, 2009 in corresponding Australian Patent Application No. 2006288208.

European Search Report dated May 26, 2010.

* cited by examiner

BODY-CAVITY IMAGE OBSERVATION APPARATUS

CROSS REFERENCE TO RELATED APPLICATION

The present application is a 35 U.S.C. §§371 national phase conversion of PCT/JP2006/317865, filed Sep. 8, 2006, which claims priority of Japanese Patent Application No. 2005-263091 filed 9 Sep. 2005, which is herein incorporated by reference.

TECHNICAL FIELD

The present invention relates to a body-cavity image observation apparatus which directly or indirectly receives body-cavity image data transmitted from a body-cavity image data transmitter such as a capsule endoscope inserted into a subject, and displays a body-cavity image based on the body-cavity image data on a display unit.

BACKGROUND ART

In recent years, a capsule endoscope equipped with an imaging function and a radio communication function has appeared in the field of an endoscope. The capsule endoscope which is inserted from a mouth into a body of a subject for an observation (examination) has a configuration to travel according to their peristalsis to capture images of the inside of organs such as the esophagus, the stomach, the small intestine, and the like (inside of the body-cavity) by using the imaging function at a predetermine imaging rate during the observation period until it is naturally excreted from the body of the subject (human body).

During the observation period when the capsule endoscope travels inside the organs, image data captured by the capsule endoscope in the body-cavity is sequentially transmitted to the outside of the subject by a radio communication function such as a radio communication, and stored in a memory provided in a receiver placed outside of the subject. The subject carrying the receiver provided with the radio communication function and the memory function can freely move without having an inconvenience even during the observation period until the capsule endoscope, after being swallowed, is excreted.

In the case of receiving image data, the receiver generally has a plurality of antennas dispersed and arranged outside of the subject for receiving an image signal transmitted from the capsule endoscope, and selectively switches to one antenna having the strongest received strength to receive the image signal. Patent Document 1, for example, discloses a receiver which performs a reception switching among the plurality of antennas arranged outside of the subject, and detects the position of the capsule endoscope inside the subject as a source of image signal transmission, based on an electric field intensity each antenna receives.

In such a capsule endoscope system, it is a common practice that the image data stored in the memory of the receiver is transferred to a work station and the like after the capsule endoscope completes the series of imaging operation, and after-the-fact perusal of images are performed. However, since a doctor or the like has a strong demand for a real-time perusal of the captured images with respect to a site of interest, sites such as the esophagus, the stomach, and the like which can be diagnosed because the capsule endoscope passes such sites in a short time after the insertion, and the like, a system including a simple image display apparatus which displays, as a body-cavity image observation apparatus, images in real-time based on a radio signal transmitted from the capsule endoscope, has been proposed.

The conventional body-cavity image observation apparatus can be electrically connected to a receiver, and includes a compact display screen and a predetermined signal processor in its simplest configuration. With such a configuration, the body-cavity image observation apparatus can receive a signal to which a receiving process is performed in the receiver, and can display the images captured by the capsule endoscope on the small display screen after performing a predetermined process based on the received signal. In such a configuration, it is possible not only to observe the captured images in real-time, but also to check a reception condition of the receiver itself since the image received by the receiver is displayed on the display unit.

Patent Document 1: Japanese Patent Application Laid-Open No. 2003-19111

DISCLOSURE OF INVENTION

Problem to be Solved by the Invention

Meanwhile, it is also conceived that the body-cavity image observation apparatus configured to have a portable size which can be grasped by an operator and to have an antenna integrated therewith, receives a radio signal directly from the capsule endoscope as changing the position of the antenna by itself, and performs an image display for the purpose of making a direct diagnosis on the spot. In this case, a cable for electrically connecting the receiver and the body-cavity image observation apparatus is not necessary, thereby enabling easier observation of the captured images in real-time.

However, since such a body-cavity image observation apparatus is capable of an image display based on a radio signal directly received by itself, and of an image display based on a radio signal received by the receiver, there may be a problem that it is impossible to recognize which radio signal the image currently displayed on the display unit is based on, in some cases.

In view of the foregoing, an object of the present invention is to provide a body-cavity image observation apparatus capable of clearly identifying whether the body-cavity image displayed on the display unit is based on the data directly received by the body-cavity image observation apparatus itself, or whether the body-cavity image displayed on the display unit is based on the data received by another receiving device.

Means for Solving Problem

A body-cavity image observation apparatus includes a first receiving unit that receives body-cavity image data directly from a body-cavity image data transmitter which is inserted into a subject; a second receiving unit that receives the body-cavity image data indirectly via another receiving device which has received the body-cavity image data from the body-cavity image data transmitter; a display unit that displays a body-cavity image based on the body-cavity image data received by the first receiving unit and the second receiving unit; and an identification notifying unit that presents different identification modes which allow a sensory recognition between a case where the body-cavity image is displayed on the display unit based on the body-cavity image data received by the first receiving unit and a case where the body-cavity image is displayed on the display unit based on the body-cavity image data received by the second receiving unit.

The body-cavity image observation apparatus according to the invention may further include a switching unit for the receiving units that selectively switches between a reception by the first receiving unit and a reception by the second receiving unit; and a display controller that controls to display the body-cavity image on the display unit based on the body-cavity image data received by the receiving unit to which the switching unit selectively switches, wherein the identification notifying unit may present different identification modes in response to the selective switching between the receiving units performed by the switching unit.

In the body-cavity image observation apparatus according to the invention, the switching unit may selectively switch a reception by the second receiving unit when the receiving device is connected to the second receiving unit via a cable which has a detachable connector.

In the body-cavity image observation apparatus according to the invention, the identification notifying unit may display different identification marks at a part of the display unit with a body-cavity image, for presenting the different identification modes.

In the body-cavity image observation apparatus according to the invention, the identification notifying unit may display an identification mark at a part of the display unit with a body-cavity image only when the body-cavity image based on the body-cavity image data received by the second receiving unit is displayed, for presenting the different identification modes.

EFFECT OF THE INVENTION

According to the present invention, the identification notifying unit presents different identification modes which allow a sensory recognition between the case where a body-cavity image based on a body-cavity image data received by the first receiving unit directly from the body-cavity image data transmitter is displayed on the display unit, and the case where a body-cavity image based on a body-cavity image data received by the second receiving unit via another receiving device is displayed on the display unit. Therefore, the body-cavity image observation apparatus has an advantage that it is possible to clearly identify which receiver has received the body-cavity image data based on which the displayed body-cavity image is displayed.

BRIEF DESCRIPTION OF DRAWINGS

FIG. 7-1 is a front view of a display example of a case where a viewer is independently used;

FIG. 7-2 is a front view of a display example of a case where the receiving device is connected;

EXPLANATIONS OF LETTERS OR NUMERALS

1 SUBJECT
2 CAPSULE ENDOSCOPE
4 RECEIVING DEVICE
5 VIEWER CABLE
5a, 5b CONNECTORS
6 VIEWER
11 DISPLAY UNIT
31 RECEIVING CIRCUIT
32 EXTERNAL INPUT TERMINAL
33 SIGNAL SELECTOR
36a SWITCHING CONTROLLER
36b DISPLAY CONTROLLER
36c IDENTIFICATION NOTIFYING UNIT
38 BODY-CAVITY IMAGE
39 CAPSULE MARK
40 BODY-CAVITY IMAGE
41 CABLE MARK

BEST MODE(S) FOR CARRYING OUT THE INVENTION

Exemplary embodiments of a body-cavity image observation apparatus according to the present invention will be explained in detail with reference to the accompanying drawings. It should be noted that the present invention is not limited to the embodiments, and various modifications may be made without departing from the scope of the invention.

Figure 1:
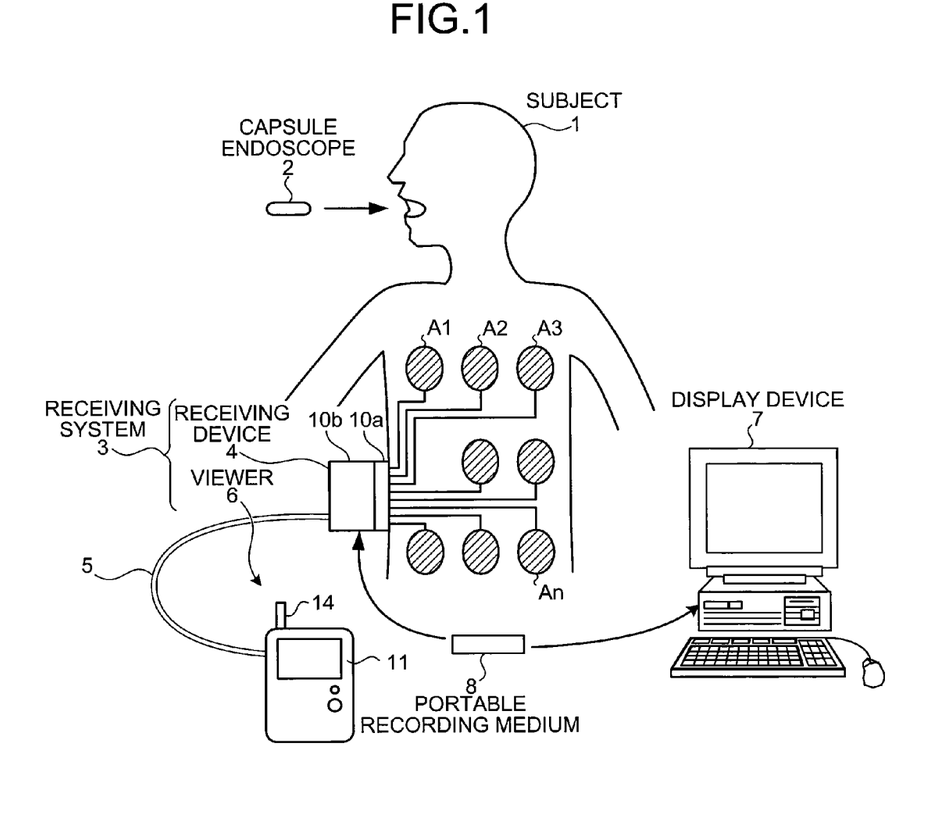
FIG. 1 is a schematic diagram of an entire configuration of a radio system for acquiring intra-subject information as a preferred embodiment of a body-cavity image observation apparatus according to the present invention.
Figure 2:
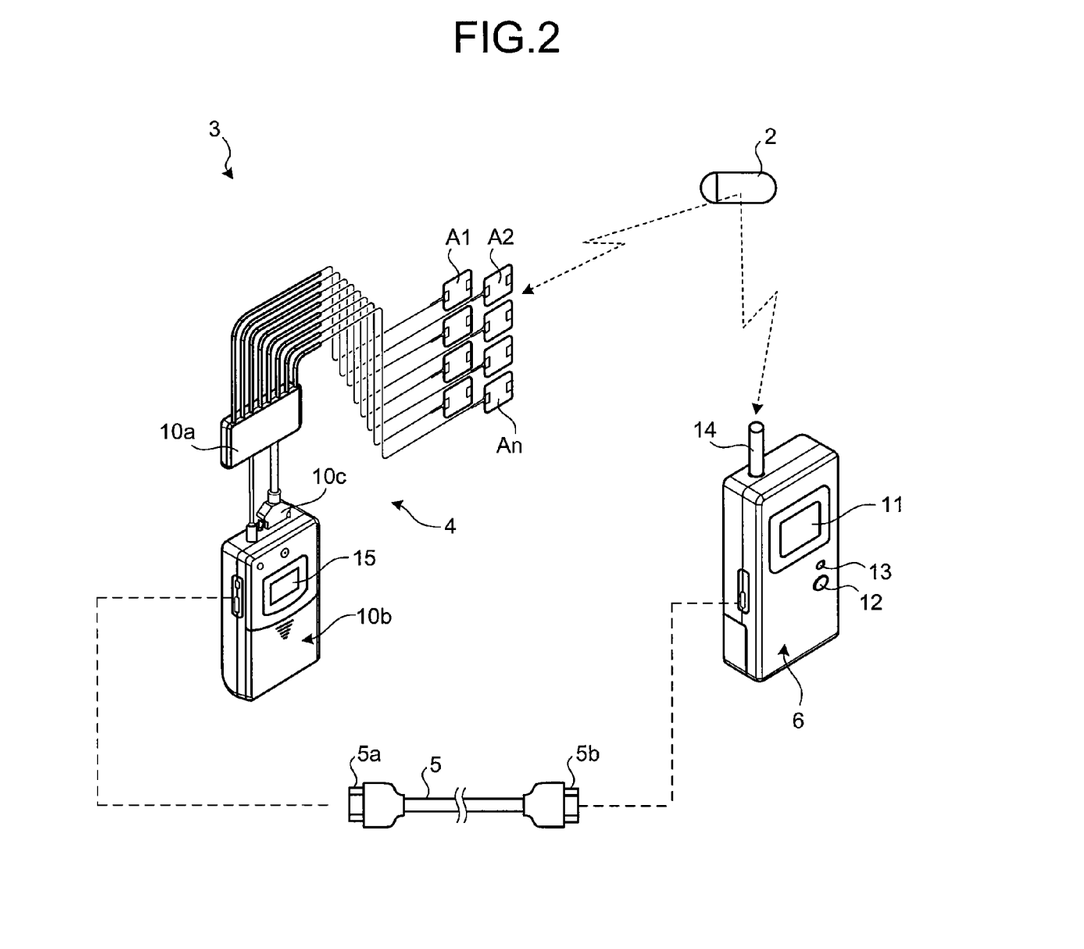
FIG. 2 is an exploded perspective view of a configuration example of a receiving system.

FIG. 1 is a schematic diagram of an entire configuration of a radio system for acquiring intra-subject information as a preferred embodiment of a body-cavity image observation apparatus according to the present invention; and FIG. 2 is an exploded perspective view of a configuration example of a receiving system in the radio system for acquiring intra-subject information. The radio system for acquiring intra-subject information uses a capsule endoscope as an example of a body-cavity image data transmitter. In FIG. 1, the radio system for acquiring intra-subject information includes a capsule endoscope 2 which captures body-cavity images to transmit data such as a video signal (body-cavity image data); and a receiving system 3 which is used for a reception processing of the radio signal transmitted from the capsule endoscope 2 inserted into a subject 1. The receiving system 3 is used in a state of being carried by the subject 1, and includes a receiving device 4 which performs a reception processing of the radio signal received from the capsule endoscope 2; and a viewer 6 which is detachably connected to the receiving device 4 via a viewer cable 5, and displays, as the body-cavity image observation apparatus, images captured by the capsule endoscope 2 based on the electric signal output from the receiving device 4.

In addition, the radio system for acquiring intra-subject information according to the embodiment includes a display device 7 which displays a body-cavity image based on a video signal received by the receiving device 4; and a portable recording medium 8 for performing data transmission between the receiving device 4 and the display device 7. The receiving device 4 includes an antenna unit 10a having a plurality of receiving antennas A1 to An to be attached on the outside surface of the subject 1; and a main receiving unit 10b as a main body of the receiving device which performs a processing of the radio signal received via the antenna unit 10a, and the units 10a and 10b can be detachably connected via a connector 10c (see FIG. 2). The receiving antennas A1 to An are provided to a receiving jacket which can be worn by the subject 1. The subject 1 may be equipped with the receiving antennas A1 to An by wearing the receiving jacket. In this case, the receiving antennas A1 to An may be detachable with respect to the jacket.

The display device 7 is for displaying body-cavity images and the like captured by the capsule endoscope 2, and has a configuration such as a work station which performs an image display based on the data obtained via the portable recording medium 8 and the like. Specifically, the display device 7 may be configured to display images directly by the CRT display, liquid crystal display, and the like, or may be configured to output images to other media.

The portable recording medium 8 employs the compact flash (registered trademark) memory and the like, is detachable with respect to the receiving device 4 and the display device 7, and has a configuration capable of outputting and recording information when attached to the both. In the embodiment, the portable recording medium 8 is attached to the display device 7 of the work station to store identification information such as an examination ID before the examination, for example. The portable recording medium 8 is attached to the receiving device 4 to make the identification information read out by the receiving device 4 to be registered in the receiving device 4. While the capsule endoscope 2 travels inside the body-cavity of the subject 1, the portable recording medium 8 is attached to the receiving device 4 which is attached to the subject 1 to record data transmitted from the capsule endoscope 2. After the capsule endoscope 2 is excreted from the subject 1, i.e., after the imaging of the inside of the subject 1 is completed, the portable recording medium 8 is removed from the receiving device 4 to be attached to the display device 7. Then, the display device 7 reads out the data recorded in the portable recording medium 8. For example, performing data transmission between the receiving device 4 and the display device 7 via the portable recording medium 8 enables the subject 1 to freely move during the imaging of the inside of the body-cavity, also contributing to a reduction in the period for the data transmission with the display device 7. Alternatively, another configuration may be employed in which data transmission between the receiving device 4 and the display device 7 is performed by using another recording device which is built in the receiving device 4 by using a hard disk for example, and the receiving device 4 and the display device 7 may be connected wirelessly or with a cable for the data transmission with the display device 7.

The viewer 6 is portable, formed to have a size which can be grasped by an operator, and has a function of displaying a body-cavity image based on the electric signal (body-cavity image data) output from the receiving device 4. To realize such function, the viewer 6 includes a display unit 11 of a compact LCD for image display. A power switch is denoted by a numeral 12, a pilot lamp which lights during the operation of the device is denoted by a numeral 13. The viewer 6 integrally includes an antenna 14 which has a rod shape and realizes a receiving function for directly receiving the radio signal (body-cavity image data) transmitted from the capsule endoscope 2 without being via the receiving device 4. In FIG. 2, the receiving device 4 and the viewer 6 are connected by the viewer cable 5 having connectors 5a and 5b. However, the receiving device 4 and the viewer 6 are not always used in a state of being connected, and the connectors 5a and 5b of the viewer cable 5 are unconnected under a condition where no real-time observation based on the image received by the receiving device 4 is performed, so that the subject 1 carries only the receiving device 4.

Next, the configuration of the receiving device 4 will be explained by using the perspective view of FIG. 2 and the block diagram of FIG. 3. The receiving device 4 has a function of receiving body-cavity image data wirelessly transmitted from the capsule endoscope 2. The receiving device 4, which is shaped to be attached to and carried by the subject 1, is composed of the antenna unit 10a and the main receiving unit 10b to which the antenna unit 10a is detachably connected via the connector 10c. The antenna unit 10a receives the radio signal transmitted from the capsule endoscope 2 via the receiving antennas A1 to An, and demodulates the radio signal to a video signal to be output, and the main receiving unit 10b performs a signal processing and the like on the video signal.

A front surface of the outside surface of the main receiving unit 10b is provided with a display unit 15 which is formed by a liquid crystal display such as the LCD serves as a display unit and a warning unit, and displays identification information such as the registered examination ID described above. A side surface of the outside surface thereof is provided with an insertion unit (not shown) for the portable recording medium 8. The insertion unit detachably retains the inserted portable recording medium 8, and enables the main receiving unit 10b to record image data.

Figure 3:
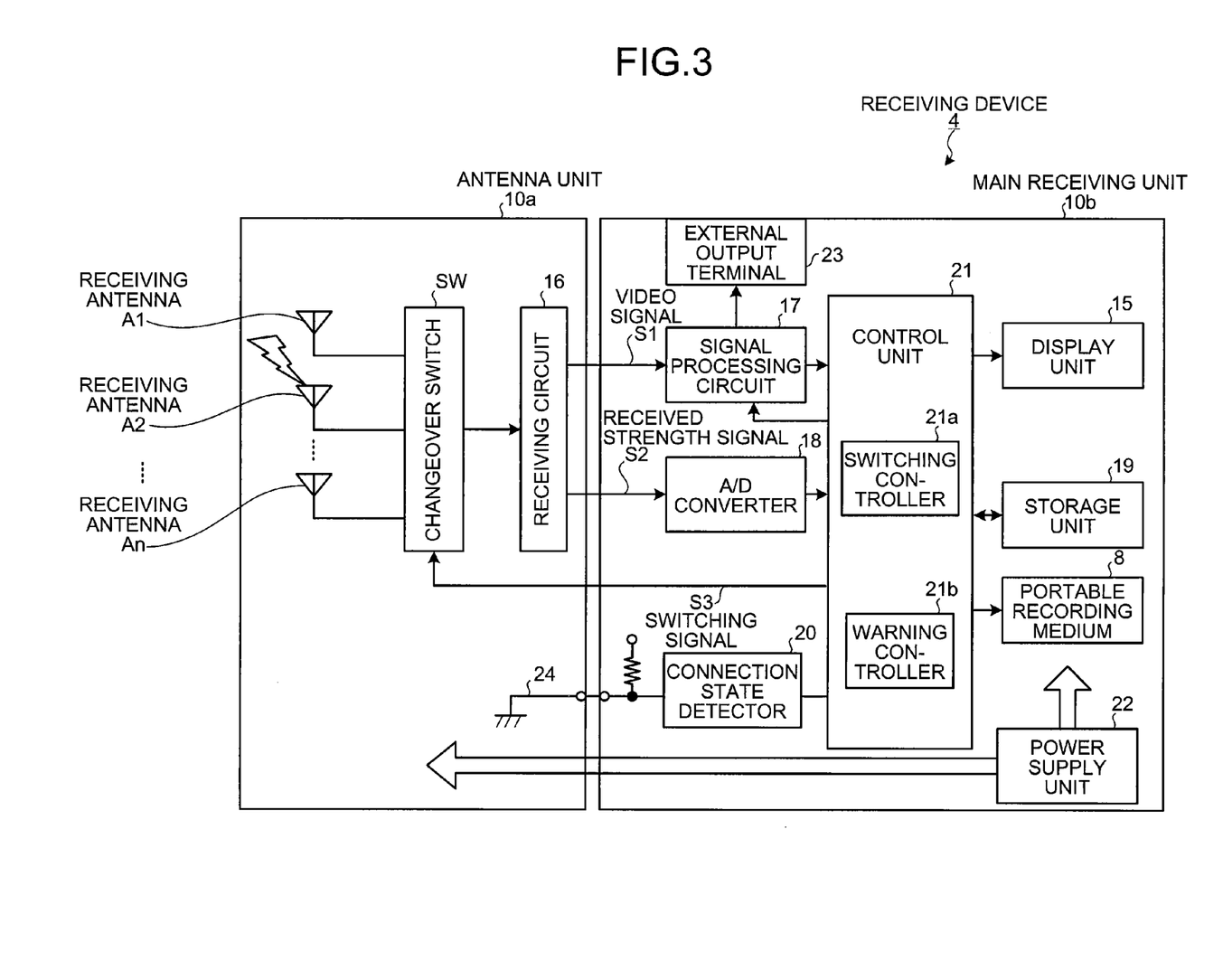
FIG. 3 is a schematic block diagram of an example of a hardware configuration of a receiving device.

As shown in FIG. 3, the antenna unit 10a includes a changeover switch SW which performs a connection changeover processing in which one of the receiving antennas A1 to An is selectively switched; and a receiving circuit 16 which is connected at a subsequent stage of the changeover switch SW, amplifies the radio signal from the receiving antennas A1 to An which is connected via the changeover by the changeover switch SW, and demodulates to a video signal as transmission information.

The main receiving unit 10b receives the video signal demodulated by the antenna unit 10a to perform a signal processing thereon. As shown in FIG. 3, the main receiving unit 10b includes a signal processing circuit 17 and an A/D converter 18 which are connected at a subsequent stage of the receiving circuit 16 via the connector 10c; the display unit 15; a storage unit 19 which stores various types of information; the portable recording medium 8; a connection state detector 20; a control unit 21 which controls such component parts; and a power supply unit 22 which performs a power supply based on a battery to the main receiving unit 10b and the antenna unit 10a.

The signal processing circuit 17 performs a signal processing such as a serial-parallel conversion, a pixel interpolation processing, and an image compression processing with respect to the video signal data which is demodulated in the receiving circuit 16 of the antenna unit 10a. The main receiving unit 10b also includes an external output terminal 23 to which the connector 5a of the viewer cable 5 is connected. The external output terminal 23, when the connector 5a is connected thereto, transmits and outputs body-cavity image data which is branched and output from the signal processing circuit 17 before the signal processing to a side of the viewer 6 via the cable 5. The control unit 21 includes a switching controller 21a that performs a switching control of an antenna; and a warning controller 21b which, as a controller, controls whether a warning display indicating that the antenna is unconnected should be performed or not to a user via the display unit 15.

The receiving circuit 16 amplifies the radio signal output from the changeover switch SW, outputs the demodulated video signal S1 to the signal processing circuit 17, and also outputs a received strength signal S2 which indicates a signal strength of the amplified radio signal to the A/D converter 18. The image data processed by the signal processing circuit 17 is stored in the portable recording medium 8 via the control unit 21. The received strength signal S2 which is converted by the A/D converter 18 to a digital signal is taken into the control unit 21. The switching controller 21a selects a receiving antenna which has received with the maximum signal strength as a receiving antenna for obtaining image data based on the received strength signal S2 obtained by sequentially switching the receiving antennas A1 to An, and also outputs a switching signal S3 which instructs to switch to the selected antenna to the changeover switch SW. The control unit 21 stores the signal strength each receiving antenna has received, being associated with the selected receiving antenna, in the portable recording medium 8 together with the image data. The stored signal strength of each receiving antenna is to be used as information for calculating the position of the capsule endoscope 2 inside the subject at the time when the image data is received.

The connection state detector 20 is for detecting whether the connector 10c of the antenna unit 10a is connected with respect to the main receiving unit 10b or not. In the embodiment, a signal line 24 for detecting a disconnection (for detecting antenna connection) is, for example, provided in the cable of the antenna unit 10a in addition to an RF signal line for the video signal S1 and the received strength signal S2 to detect being connected/unconnected (the antenna being unconnected) based on the level condition of the signal line 24. For example in the embodiment, the connection state detector 20 detects it as a connected state when the level of the signal line 24 is L level, and detects it as an unconnected state (antenna being unconnected) when the level of the signal line 24 is H level.

Figure 4:
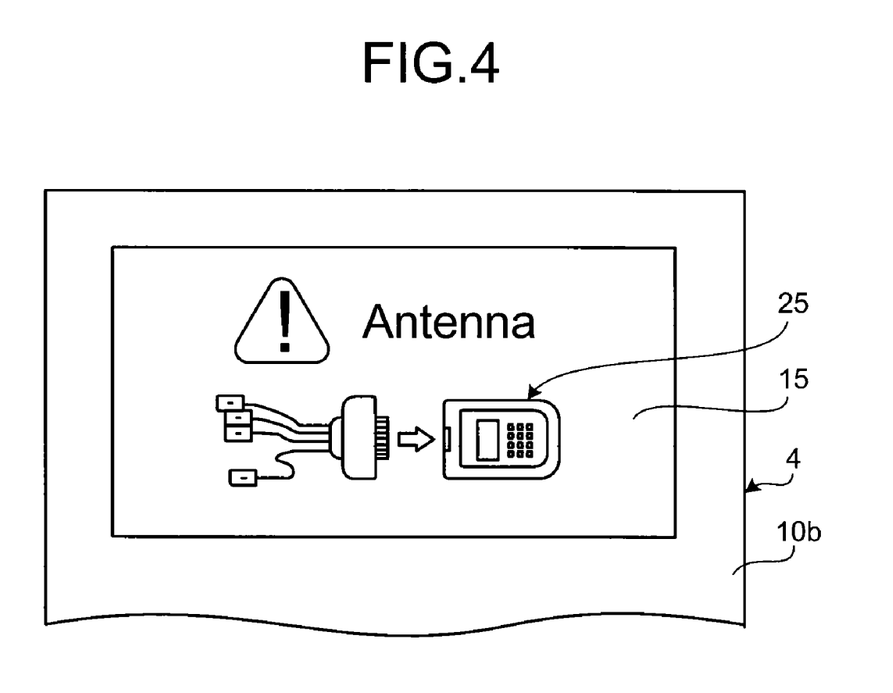
FIG. 4 is a front view of an example of a warning display which indicates that an antenna is unconnected in the receiving device.

When the connection state detector 20 detects that the antenna is unconnected under a predetermined condition, the warning controller 21b controls the display of the display unit 15 to issue a warning by a warning display of a pattern 25 which indicates the antenna being unconnected as shown in FIG. 4, for example.

Here, the predetermined condition under which whether the warning should be issued or not is determined is judged depending on whether the condition of using the antennas A1 to An during the flow of the examination by the capsule endoscope 2 is necessary or not. First of all prior to the start of the examination, patient data is set to the storage unit 19 and the like of the main receiving unit 10b, and then the antennas A1 to An are attached and set to predetermined portions of the subject 1. At this stage, it is a normal state even when the antenna unit 10a is unconnected with respect to the main receiving unit 10b (to put it the other way around, the antenna unit 10a is configured to be detachable with respect to the main receiving unit 10b by taking the workability in such an operation into consideration). After that, the connector 10c of the antenna unit 10a is attached to the main receiving unit 10b to make a connected state, and the examination is started. After the examination is started, the main receiving unit 10b receives body-cavity image data wirelessly transmitted form the capsule endoscope 2 via the antennas A1 to An, and sequentially records in the portable recording medium 8. It is an abnormal state when the antenna is unconnected (the connector 10c is unconnected) due to some causes at this stage.

In other words, it is not appropriate to issue a warning before the start of the examination (start to obtain body-cavity image data) even when the antenna is unconnected. Therefore, in the embodiment, the warning is configured to be issued as an abnormal state when the antenna is unconnected after the start of the examination in which the antennas should be necessarily used. An example of the warning control in the case where the antenna is unconnected in the embodiment will be explained with reference to the schematic flowchart shown in FIG. 5. This processing is executed under the condition where the power switch of the receiving device 4 (the main receiving unit 10b) is turned on ("Yes" at step S100). Next, for determining whether the examination is started or not, it is determined whether a recording operation has started or not (step S101). As an example of this determination processing for example, it is determined to be before the start of the recording operation at a stage where a synchronous signal for a trigger is not detected among the radio signals transmitted from the capsule endoscope 2 after the power is turned on ("No" at step S101), while once the synchronous signal is detected, it is determined to be after the start of the recording operation ("Yes" at step S101). Since the format of the portable recording medium 8 is initialized before the start of the examination, the determination of being before the start of the recording operation may be made, by checking a writing status in the portable recording medium 8, at a stage where no body-cavity image data has been written to the portable recording medium 8. Since it is normal state even when the antenna is unconnected, and no warning is necessary to be issued to the user in the case where the determination of being before the start of the recording operation is made ("No" at step S101), the display unit 15 is controlled not to perform the warning display (step S102).

Figure 5:
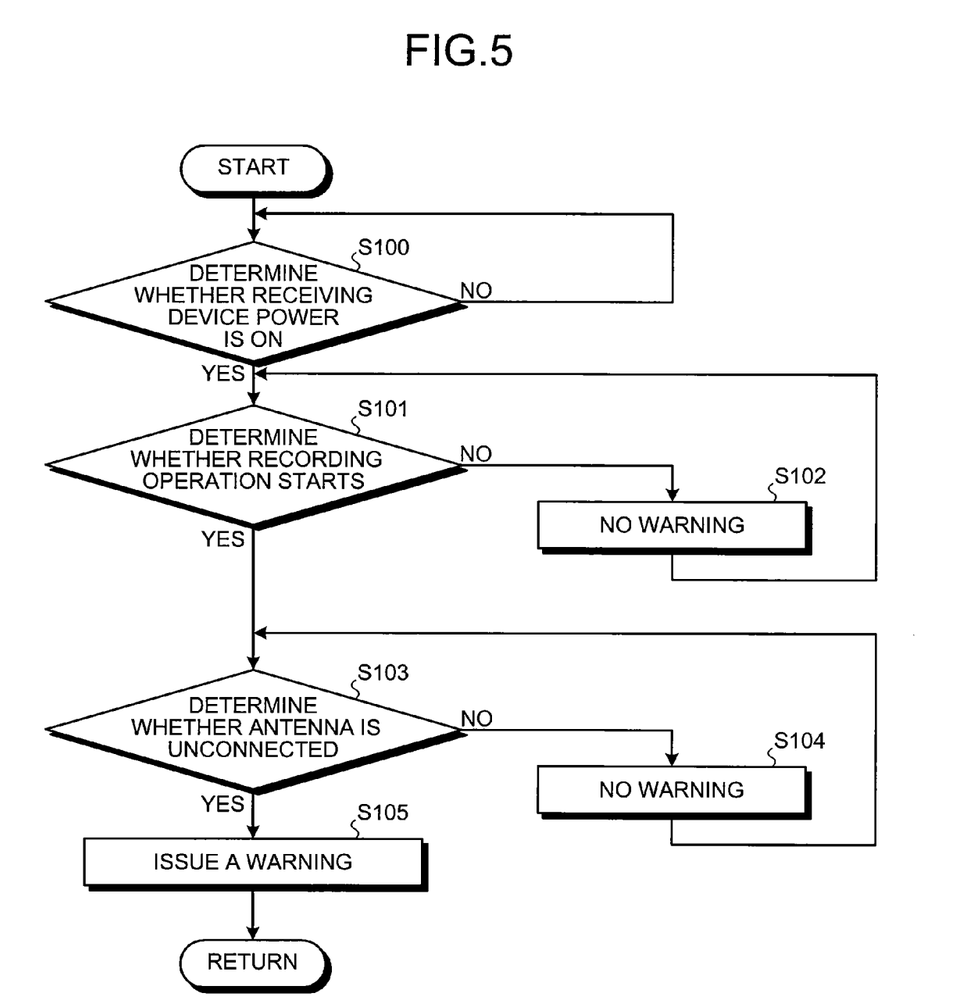
FIG. 5 is a schematic flowchart of an example of a processing control of the warning display.

On the other hand, in the case where the determination of being after the start of the recording operation ("Yes" at step S101) is made, it is determined whether the connector 10c of the antenna unit 10a is in an unconnected state (in a state where the antenna is unconnected) by referring to the detection result by the connection state detector 20 (step S103). Since it is a normal state and no warning is necessary to be issued to the user when the antenna is connected ("No" at step S103), the display unit 15 is controlled not to perform the warning display (step S104). Since it is an abnormal state when the antenna is unconnected ("Yes" at step S103), the display unit 15 is operated and controlled to issue a warning with the warning display of the pattern 25 indicating that the antenna is unconnected (step S105). By this, the user (the subject 1, a doctor, a nurse, or the like) can take a quick and appropriate measure of re-connecting the connector 10c of the antenna unit 10a to the main receiving unit 10b and the like, so that data loss in the case where the antenna is unconnected can be reduced as much as possible.

The order of the determination of the start of recording operation (step S101) and the determination of the antenna being unconnected (step S103) may be reverse, and the determination of the antenna being unconnected may be performed first. The warning for the unconnected antenna is not limited to the warning display by the display unit 15, and the warning may be made with lighting or blinking by using a light emitting element such as LED, for example. Alternatively, the warning may be made with a warning sound by using a buzzer, a speaker, and the like. Furthermore, the warning may be made by vibrating the main receiving unit 10b with a transducer and the like built in the main receiving unit 10b.

Figure 6:
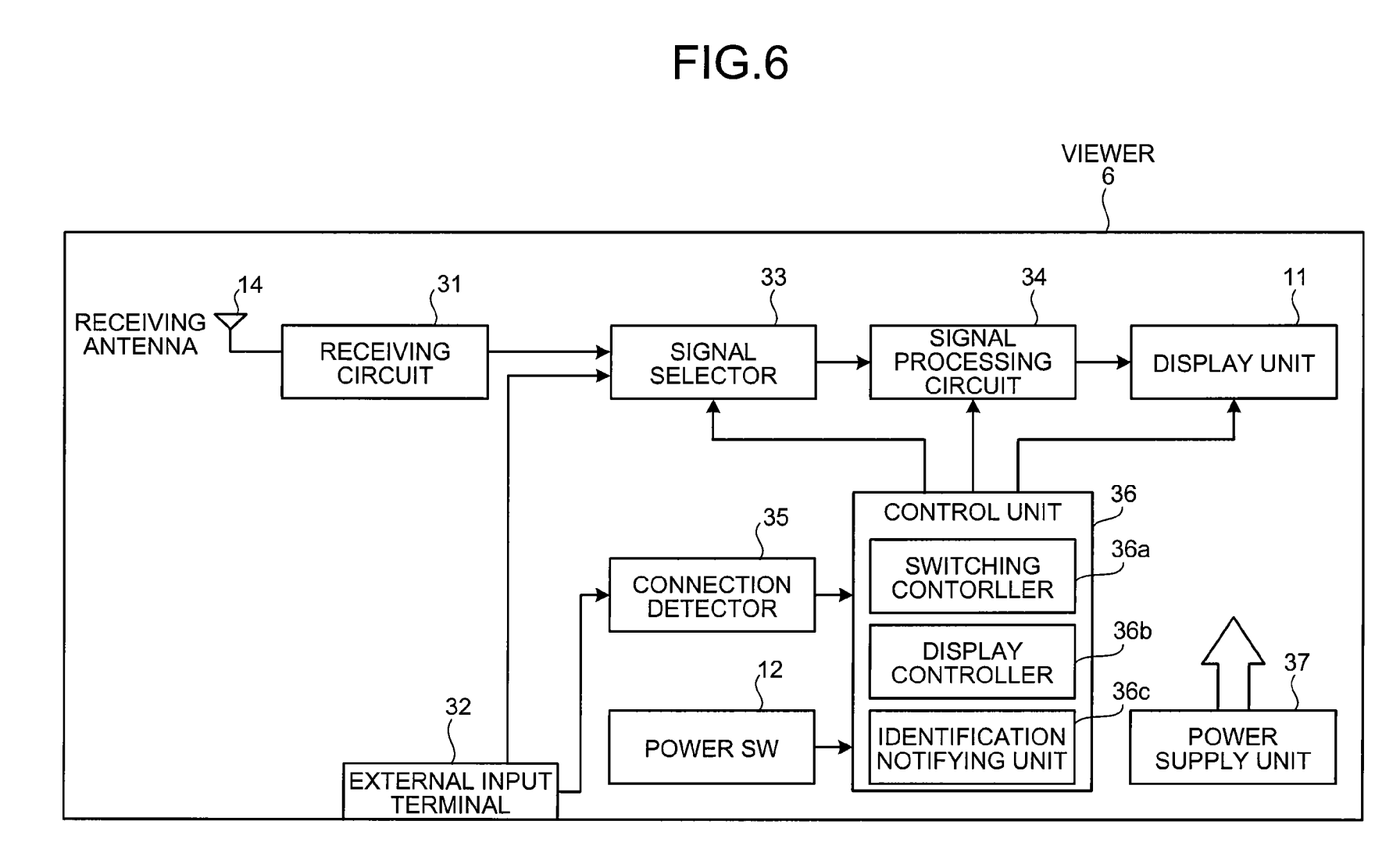
FIG. 6 is a schematic block diagram of an example of a hardware configuration of a viewer.

Next, a hardware configuration of the viewer 6 will be explained by using the block diagram in FIG. 6. As shown in FIG. 6, the viewer 6 includes a receiving circuit 31 connected to the receiving antenna 14; an external input terminal 32; a signal selector 33; a signal processing circuit 34; the display unit 11; a connection detector 35; a control nit 36 which controls such component parts; and a power supply unit 37 which supplies power to the component parts based on a battery. The control unit 36 includes a switching controller 36a that performs a switching control of the signal selector 33; a display controller 36b that performs a display control of the display unit 11; and an identification notifying unit 36c that makes the user to display an identification mark via the display unit 11.

The receiving circuit 31 is for amplifying the radio signal which the receiving antenna 14 has received directly from the capsule endoscope 2 and for demodulating as a video signal representing body-cavity image data, and functions as a first receiving unit that directly receives body-cavity image data from the capsule endoscope 2. The external input terminal 32, to which the connector 5b of the viewer cable 5 is detachably connected, functions as a second receiving unit that indirectly receives the body-cavity image data which the receiving device 4 has received from the capsule endoscope 2 via the receiving device 4. The connection detector 35 detects whether the receiving device 4 is connected or not with respect to the external input terminal 32 via the viewer cable 5, and outputs the detected signal to the control unit 36. The switching controller 36a is for outputting a switching signal to the signal selector 33 so that a reception of the body-cavity image data based on the receiving circuit 31 and a reception of the body-cavity image data via the external input terminal 32 are selectively switched based on the detected signal from the connection detector 35, and functions as a switching unit for receiving units together with the signal selector 33. In the embodiment, the switching controller 36a controls the signal selector 33 to selectively switch to the reception by the external input terminal 32 in the case where the receiving device 4 to which the connector 5b of the viewer cable 5 is connected is connected to the external input terminal 32, while controls the signal selector 33 to selectively switch to the reception by the receiving circuit 31 in the case where the viewer 6 is in a state of being independent.

The signal processing circuit 34 performs a signal processing such as a serial-parallel conversion, a pixel interpolation processing, and an image compression processing with respect to either, which is selected by the signal selector 33, of the video signal data demodulated in the receiving circuit 31, or of the video signal data obtained form the receiving device 4 via the external input terminal 32. The display controller 36b performs a processing for controlling to display the body-cavity image based on the body-cavity image data received by either, to which the signal selector 33 has selectively switched, of the receiving circuit 31 or the external input terminal 32 on the display unit 11.

The identification notifying unit 36c displays different identification modes which can be visually recognized, respectively for the case where the body-cavity image based on the body-cavity image data received by the receiving circuit 31 is displayed on the display unit 11, and the case where the body-cavity image based on the body-cavity image data received via the external input terminal 32 is displayed. In other words, the identification notifying unit 36c makes the display unit 11 display identification marks which can be recognized between the case where the body-cavity image which the viewer 6 has received directly form the capsule endoscope 2 independently is displayed, and the case where the body-cavity image which the receiving device 4 has received from the capsule endoscope 2 is indirectly displayed in real-time on the display unit 11 of the viewer 6.

Figure 71:
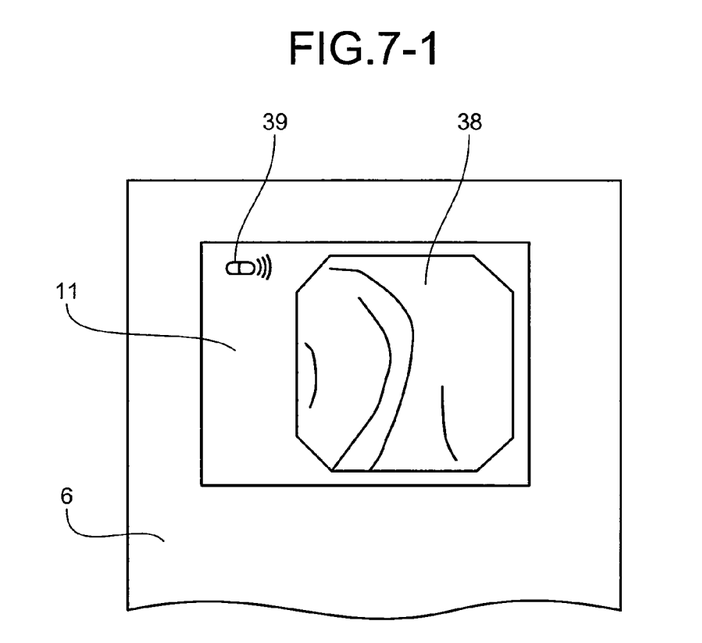
Figure 72:
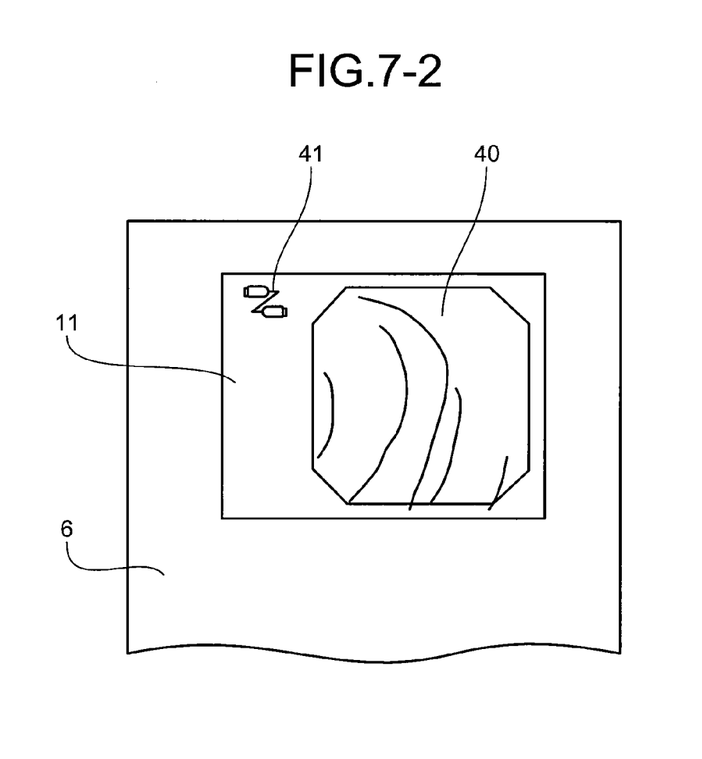

As one example in the embodiment, in the case where a body-cavity image 38 based on the body-cavity image data which the viewer 6 has received directly from the capsule endoscope 2 independently is displayed on the display unit 11, the identification notifying unit 36c displays an identification mark of a capsule mark 39 at a part of the display unit 11 together with the body-cavity image 38 as a first identification mode which allows recognizing that the image wirelessly received directly from the capsule endoscope 2 is displayed, as shown in FIG. 7-1, for example. In the case where a body-cavity image 40 based on the body-cavity image data which the receiving device 4 has received from the capsule endoscope 2 in a state where the receiving device 4 is connected via the viewer cable 5 is displayed on the display unit 11, the identification notifying unit 36c displays an identification mark of a cable mark 41 at a part of the display unit 11 together with the body-cavity image 40 as a second identification mode which allows recognizing that the image wirelessly received by the receiving device 4 to which the viewer cable 5 is connected is displayed, as shown in FIG. 7-2, for example.

Figure 8:
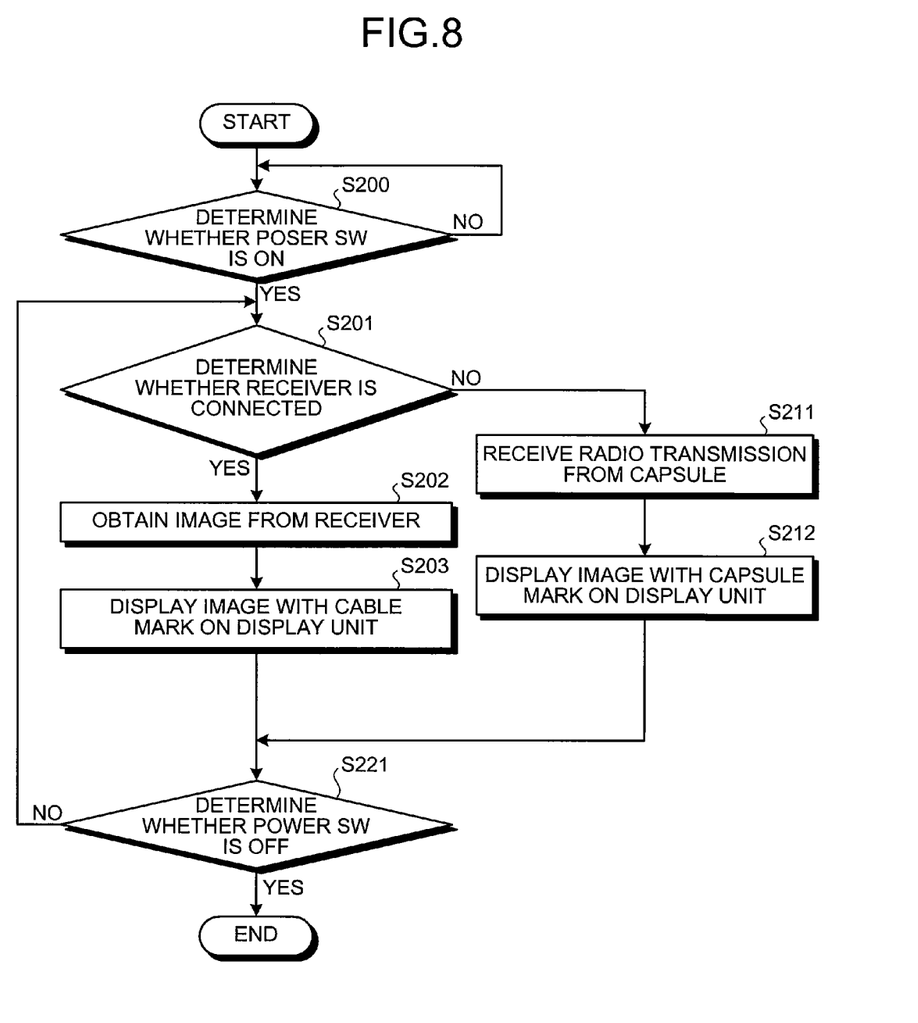
FIG. 8 is a schematic flowchart of an example of a processing control for a display control and an identification notification.

FIG. 8 is a schematic flowchart of an example of the above-described operation control which is executed by the display controller 36b and the identification notifying unit 36c of the control unit 36 depending on the connection status of the receiving device 4 (receiver). The processing control is executed in a state where the power switch 12 of the viewer 6 is turned on ("Yes" at step S200). First, it is determined whether the receiver (the receiving device 4) is connected or not based on the detection result of the connection detector 35 (step S201). When the receiving device 4 is connected via the viewer cable 5 ("Yes" at step S201), the viewer 6 functions as a monitor of the receiving device 4, obtains body-cavity image data in real-time via the viewer cable 5 and the external input terminal 32 from the receiving device 4 (step S202), and displays the body-cavity image 40 based on the obtained body-cavity image data on the display unit 11 in real-time. At the same time, the viewer 6 displays the identification mark of the cable mark 41 at a part of the display unit 11 together with the body-cavity image 40 (step S203).

On the other hand, when the receiving device 4 is not connected ("No" at step S201), the radio signal from the capsule endoscope 2 is directly received via the receiving antenna 14 (step S211). Then, the body-cavity image 38 based on the body-cavity image data obtained via the direct reception is displayed on the display unit 11, and the identification mark of the capsule mark 39 is displayed at a part of the display unit 11 together with the body-cavity image 38 at the same time (step S212). These processing controls are repeated until the power switch 12 is turned off ("Yes" at step S221).

As shown in FIG. 1, for example, in the case where the receiving device 4 and the viewer 6 are connected via the viewer cable 5 to perform a real-time observation by using the viewer 6 as a monitor of the receiving device 4, since the identification mark of the cable mark 41 is also displayed on the display unit 11 as shown in FIG. 7-2 when the body-cavity image 40 based on the body-cavity image data which the receiving device 4 has received from the capsule endoscope 2 is displayed on the display unit 11, it is clear that the displayed body-cavity image 40 is an image which the receiving device 4 has received from the capsule endoscope 2.

Figure 9:
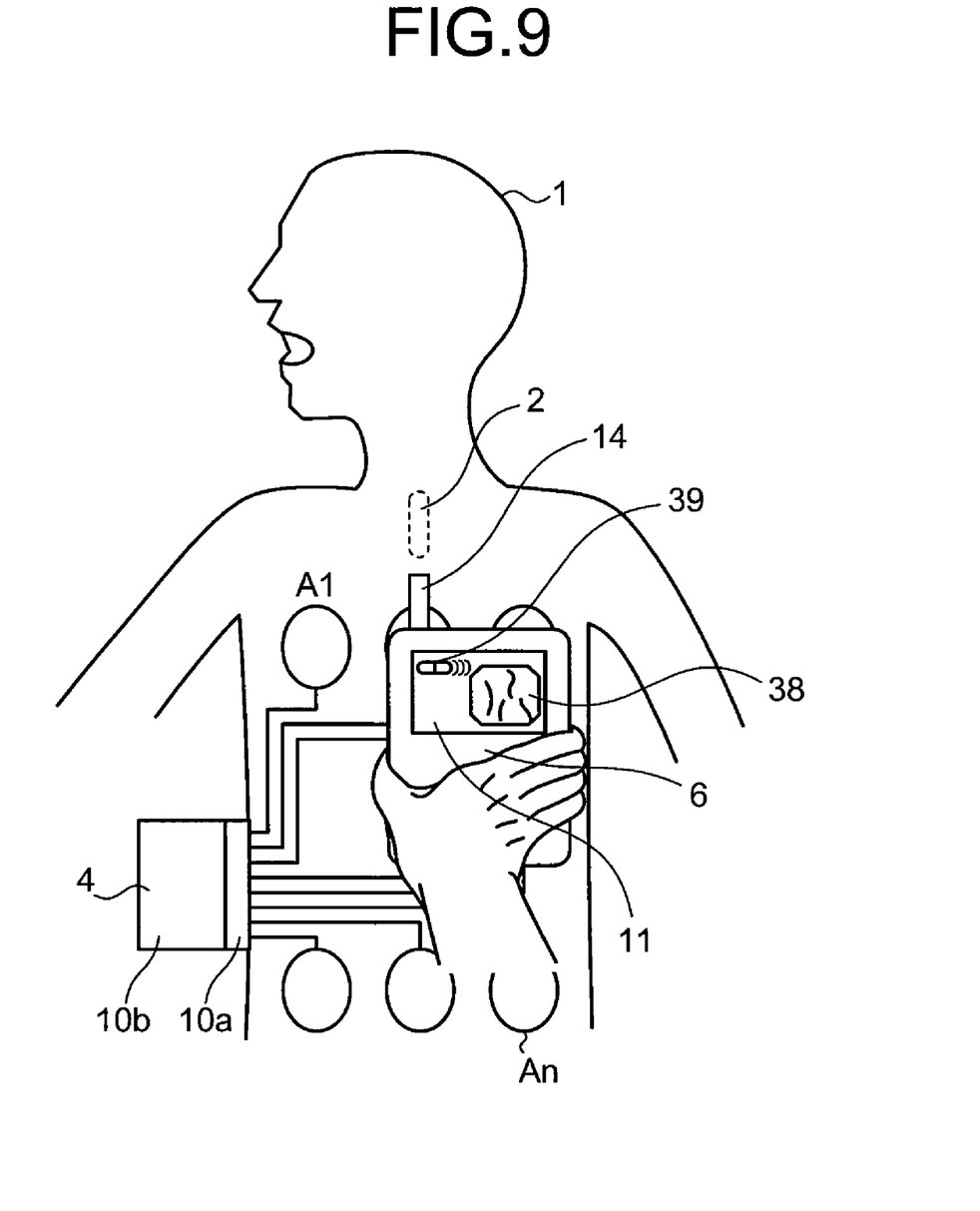
FIG. 9 is a front view of an example of an independent usage of the viewer.

In addition, if the doctor grasps the viewer 6 in an independent state and brings it close to the subject 1, as shown in FIG.

9, to receive the radio signal from the capsule endoscope 2 via the receiving antenna 14 subsidiarily and directly in parallel with the receiving antennas A1 to An when the capsule endoscope 2 passes through portions such as the esophagus, the stomach, and the like as necessary for example, it is possible to directly obtain body-cavity image data which has not passed through the receiving device 4, and to display on the display unit 11 of the viewer 6 as the body-cavity image 38. At this time, since the identification mark of the capsule mark 39 is also displayed on the display unit 11 as shown in FIG. 7-1, it is clear that the displayed body-cavity image 38 is an image which the viewer 6 itself has received directly from the capsule endoscope 2. Thus, it is possible to obtain good images and to perform, by changing the position of the viewer 6 and moving the position of the receiving antenna 14 while seeing the body-cavity image 38, subsidiary observation for supplementing the genuine observation using the receiving device 4 well.

In the embodiment, different identification marks, i.e., the capsule mark 39 and the cable mark 41, are displayed on the display unit 11 for the case of using the viewer 6 independently, and the case of connecting the receiving device 4, respectively. However, it is satisfactory as long as the case of using viewer 6 independently and the case of connecting the receiving device 4 have different identification modes, respectively. For example, while no capsule mark 39 may be displayed on the display unit 11 in the case of using the viewer 6 independently, the cable mark 41 may be displayed on the display unit 11 only in the case of connecting the receiving device 4, so that both cases can be identified with each other. In addition, the visually different identification modes are not limited to the display by the display unit 11, and may be present in other way such as lighting or blinking display using a light emitting element such as the LED for the case of using the viewer 6 independently, and the case of connecting the receiving device 4, respectively. For example, the LED is arranged outside the display unit 11 with a notation "cable is connected" and the like attached thereto, and thereby the lighting of the LED while the receiving device 4 is connected may be configured to indicate that the cable is connected. The different identification modes for the case of using the viewer 6 independently and the case of connecting the receiving device 4 are not limited to modes like a display which allows visual recognition, and may be any sensory recognizable modes. For example, it may be auditory recognizable modes based on different audio outputs by using speaker and the like.

INDUSTRIAL APPLICABILITY

As described, the body-cavity image observation apparatus according to the present invention is useful in the case where body-cavity image data transmitted from a body-cavity image data transmitter such as a capsule endoscope and the like inserted into a subject is directly or indirectly received by the body-cavity image observation apparatus, and the body-cavity image based on the body-cavity image data is displayed on a display unit, specifically suitable for the case where an image display based on a radio signal directly received by the body-cavity image observation apparatus itself and an image display based on a radio signal received by a receiver are possible.

The invention claimed is:

1. A body-cavity image observation apparatus, comprising:
   a capsule endoscope configured to capture body-cavity image data and to transmit the body-cavity image data when the capsule endoscope travels inside a body-cavity of a subject;
   a receiving device configured to perform a reception processing of the body-cavity image data transmitted from the capsule endoscope; and
   a viewer configured to be detachably connected to the receiving device and having a display device configured to display the body-cavity image data captured by the capsule endoscope, wherein
   the viewer includes:
   an antenna for directly receiving the body-cavity image data transmitted from the capsule endoscope, without transmission from the receiving device;
   a switching controller configured to selectively switch between a reception by the receiving device, when the viewer is connected to the receiving device, and a reception by the viewer when the viewer is not connected to the receiving device; and
   an identification notifying unit configured to present different identification modes which allow a sensory recognition between a case where the body-cavity image is displayed on the display device, based on the body-cavity image data received directly by the viewer, and a case where the body-cavity image is displayed on the display device, based on the body-cavity image data received by the receiving device and transmitted to the viewer.

2. The body-cavity image observation apparatus according to claim 1, wherein the identification notifying unit displays different identification marks at a part of the display device with a body-cavity image, for presenting the different identification modes.

3. The body-cavity image observation apparatus according to claim 1, wherein the identification notifying unit displays an identification mark at a part of the display device with a body-cavity image only when the body-cavity image based on the body-cavity image data received by the receiving device is displayed, for presenting the different identification modes.

4. The body-cavity image observation apparatus according to claim 1, wherein the receiving device and the viewer are operatively connectable via a detachable connector.

* * * * *